United States Patent [19]
O'Mahony et al.

[11] Patent Number: 5,632,270
[45] Date of Patent: May 27, 1997

[54] METHOD AND APPARATUS FOR CONTROL OF LUNG VENTILATOR EXHALATION CIRCUIT

[75] Inventors: John J. O'Mahony, Galway, Ireland; Floyd R. Farnham, III, Encinitas, Calif.

[73] Assignee: Puritan-Bennett Corporation, Overland Park, Kans.

[21] Appl. No.: 304,048

[22] Filed: Sep. 12, 1994

[51] Int. Cl.$^6$ .................................................. A61M 16/00
[52] U.S. Cl. ........................ 128/204.24; 128/204.21; 128/204.23; 128/205.24
[58] Field of Search .............. 128/204.24, 204.21, 128/204.23, 204.26, 205.24

[56] References Cited

U.S. PATENT DOCUMENTS

| | | | |
|---|---|---|---|
| 4,637,386 | 1/1987 | Baum | 128/204.21 |
| 4,805,612 | 2/1989 | Jensen | 128/205.24 |
| 4,838,257 | 6/1989 | Hatch | 128/204.21 |
| 4,905,687 | 3/1990 | Ponkala . | |
| 5,040,529 | 8/1991 | Zalkin | 128/204.21 |
| 5,127,400 | 7/1992 | DeVries et al. | 128/205.24 |
| 5,303,699 | 4/1994 | Bonessa et al. | 128/204.21 |
| 5,339,807 | 8/1994 | Carter | 128/205.24 |
| 5,373,842 | 12/1994 | Olsson et al. | 128/204.21 |
| 5,433,193 | 7/1995 | Sanders et al. | 128/204.21 |

FOREIGN PATENT DOCUMENTS

| | | |
|---|---|---|
| 0190856 | 8/1986 | European Pat. Off. . |
| 0309633 | 4/1989 | European Pat. Off. . |
| 2695830 | 3/1994 | France . |

*Primary Examiner*—Vincent Millin
*Assistant Examiner*—William J. Deane, Jr.
*Attorney, Agent, or Firm*—Fulwider Patton Lee & Utecht, LLP

[57] ABSTRACT

Patient airway baseline pressure levels are controlled in a ventilator having a pneumatically controlled exhalation valve without an external supply of pilot pressure, by supplying an internal source of controllable pilot pressure for operating the exhalation valve. The pressure of pressurized air supplied by an internal pump can be electrically controlled by pulse width modulation of a variable pulse duration signal. A second source of pressurized air for pilot pressure is provided, and in one embodiment is a reservoir provided for receiving pressurized air from the pump and from the exhalation circuit. A valve is connected to the pump means and the reservoir for receiving pressurized air from the pump in a first position, and for receiving pressurized air from the reservoir in a second position. When the valve means is in the second position, pressurized air is delivered at a pressure which is the greater of the pressurized air supplied by the pump means or the gas flow from the exhalation circuit.

10 Claims, 3 Drawing Sheets

METHOD AND APPARATUS FOR CONTROL OF LUNG VENTILATOR EXHALATION CIRCUIT

BACKGROUND OF THE INVENTION

1. Field of the Invention

This invention relates generally to breathing ventilators, and more particularly relates to a system and method for providing pilot pressure to a pneumatically controlled exhalation valve utilized for controlling patient end expiratory pressure (PEEP) during the expiratory cycle of a breath, and for closing the exhalation valve during inspiration, in a ventilator system having a limited air supply and having no external compressed air source for operation of the pneumatically controlled exhalation valve.

2. Description of Related Art

Medical ventilators are generally designed to ventilate a patient's lungs with breathing gas to assist a patient in breathing when the patient is somehow unable to adequately breath without assistance. Pressure assistance can be instituted when the patient has already begun an inspiratory effort, typically by bellows or fixed volume piston type ventilators. With such a system, it is desirable to immediately increase the pressure after a breath is initiated in order to reach a target pressure. This rise in pressure causes flow to be initiated in the patient airway which supplies breathing gas to the patient's lungs. Conventional pressure controlled ventilator systems terminate or reduce the flow when the target pressure is reached to limit the patient airway pressure. Patient airway pressure can be finely controlled by an exhalation valve that is typically operated by a pilot pressure supplied pressurized breathing gas from the ventilator or an external supply of pressurized or compressed air. For purposes of this description, the terms "compressed" and "pressurized" air are intended to mean any air or gas that has a pressure greater than atmospheric pressure that can be utilized as a source of pilot pressure for operation of the pilot pressure driven exhalation valve.

However, some ventilators, such as piston type ventilators for example, are generally designed to provide pressurized breathing gas on demand, and therefore are not generally suited to provide a constant supply of pilot pressure for operation of a pneumatically controlled exhalation valve. Provision of an additional supply of compressed air for operation of the pneumatically controlled exhalation valve, such as by a tank of compressed air, or an external compressor, can add significantly to the complexity, size and weight of a ventilator system, negating advantages of compactness and efficiency of a piston type ventilator. For piston type ventilator systems that are operated in emergency vehicles, or that are portable, such an external source of compressed air may not be readily available. Conventional piston type ventilators therefore commonly do not provide sufficient control of the patient airway baseline pressure, commonly known as PEEP (patient end expiratory pressure), suitable for use of such ventilators for intensive care patients. patients, it is often desirable to provide the capability of controlling and changing the PEEP during different phases of patient breathing, such as for APRV (airway pressure relief ventilation) in which two baseline pressure levels are cycled at a fixed rate in time with a constant flow rate, and a programmed cycle of patient airway pressure is superimposed over the preset baseline pressures. It would therefore be desirable to provide a method and apparatus for supplying an internal source of controllable pilot pressure for operating a pneumatically controlled exhalation valve of a piston type ventilator, allowing for PEEP to be controlled to provide APRV.

SUMMARY OF THE INVENTION

Briefly, and in general terms, the present invention provides for a method and apparatus for controlling patient airway baseline pressure levels in a ventilator having a pneumatically controlled exhalation valve, by supplying an internal source of controllable pilot pressure for operating the exhalation valve.

Accordingly, the present invention provides for an apparatus for controlling gas flow through an exhalation circuit of a lung ventilator having a limited pressurized air supply, in order to control airway pressure in a patient airway connected to the exhalation circuit. The apparatus includes a pneumatically operated exhalation valve for controlling flow of gas through the exhalation circuit, such as to maintain PEEP, responsive to pilot pressure supplied to the exhalation valve through a pilot pressure line, pump means for supplying a source of pressurized air, and control means for controlling the pressure of pressurized air supplied by the pump means. The pump means preferably comprises a vibrating armature type of pump actuated by a variable pulse duration signal at a constant frequency, generated by a pulse width modulation means, allowing for electrical control of the pump, and pilot pressure delivered to the exhalation valve. The control means preferably also includes pressure sensor means, and is preferably responsive to pressure produced by the pump to provide feedback control of the pressure of the pressurized air supplied by the pump.

During the inhalation portion of a breath cycle, greater force may be required to operate the exhalation valve than during the exhalation portion of a breath cycle, and thus a second source of pressurized air for use as pilot pressure for operating the exhalation valve is also provided. In one preferred embodiment, the second source of pressurized air comprises a reservoir of pressurized air received from the pump and from the exhalation circuit. Valve means are connected to the pump means and the reservoir, the valve means having a first position in fluid communication with the pump means for receiving pressurized air from the pump means, and a second position in fluid communication with the reservoir for receiving pressurized air from the reservoir. The valve means is connected to the exhalation valve to deliver pressurized air to the exhalation valve from either the pump or the exhalation circuit as pilot pressure for operation of the exhalation valve. Valve control means are also provided for switching the valve means between the first and second positions.

The reservoir preferably includes first inlet and second inlets, each including a check valve permitting flow of the greater pressure of pressurized air into the reservoir from the pump and the exhalation circuit, such that when the valve means is in the second position, pressurized air is delivered at the greater pressure of the pressurized air supplied by the pump means or the gas flow from the exhalation circuit.

The invention also provides for a method of controlling gas flow by controlling the pressure of pressurized air supplied by the pump means, and switching the valve means between the first and second positions, such that when the valve means is in the first position, the exhalation valve is operated by pilot pressure supplied by the pump means, and such that when the valve means is in the second position, the exhalation valve is operated by pilot pressure from the second source of pressurized air. In another preferred aspect of the method, the step of controlling the pressure of pressurized air supplied by the pump means comprises generating a variable pulse duration actuation signal at a constant frequency for actuating the pump means, and controlling the duration of the variable pulse duration actuation signal. In another preferred aspect of the method, the valve means is switched to the first position during an exhalation portion of a breathing cycle of the ventilator, and the valve means is switched to the second position during an inhalation portion of a breathing cycle of the ventilator.

These and other aspects and advantages of the invention will become apparent from the following detailed description, and the accompanying drawing, which illustrates by way of example the features of the invention.

DETAILED DESCRIPTION OF THE PREFERRED EMBODIMENTS

Some ventilators, such as piston type ventilators for example, while generally quite adequate for providing pressurized breathing gas on demand, are not able to provide a constant supply of pilot pressure for operation of a pneumatically controlled exhalation valve, without provision of an external source of pressurized air, which can add significantly to the complexity, size and weight of a ventilator system. Conventional piston type ventilators do not provide sufficient control of PEEP for intensive care patients.

Figure 1:
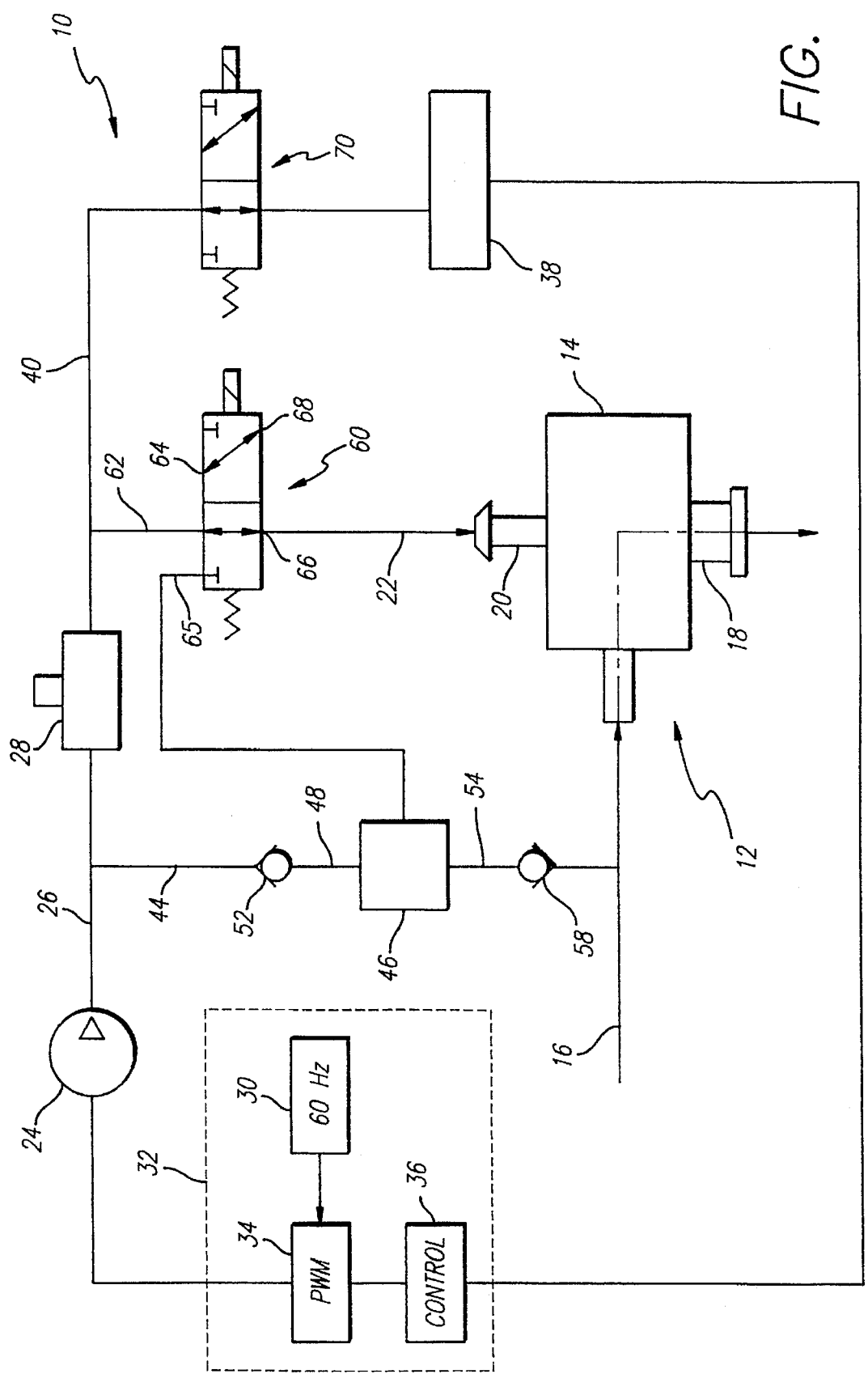
FIG. 1 is a diagram of a first embodiment of the apparatus of the invention for controlling a lung ventilator exhalation circuit.

As is illustrated in FIG. 1, the invention is embodied in an apparatus 10 for controlling gas flow through an exhalation circuit 12 of a lung ventilator having a limited capacity for providing a pressurized air supply, for controlling a pneumatically operated exhalation valve 14 controlling airway pressure in a patient airway connected to the exhalation circuit. Pressure of breathing gas in the patient airway is moderated by the pneumatically operated exhalation valve, which receives a flow of breathing gas and exhaled gas from the patient airway via exhalation line 16, and vents the breathing gas through an outlet 18. The exhalation valve is preferably a force balance type of exhalation valve, receiving a pneumatic pilot flow through inlet 20, connected to the pilot pressure line 22. The pneumatically operated exhalation valve is responsive to pilot pressure supplied through the pilot pressure line for regulating the flow of gas through the exhalation circuit.

In such a force balance type of exhalation valve, the diameter of the airway passage of the exhalation limb tubing at the valve seat, $D_{aw}$, should be less than the diameter, $D_2$, of the closure member of the valve, and the cross-sectional area of the exhalation line of the patient airway, $Area_{aw}$, should be less than the area of the closure member of the valve, $Area_{D2}$, for effective sealing and operation of the exhalation valve. The force presented by the pressure in exhalation limb of the patient airway to open the exhalation valve ($force_{open}$) is equal to the pressure in the exhalation limb of the patient airway ($P_{aw}$) multiplied by the $Area_{aw}$. The force to close the exhalation valve ($force_{close}$) is equal to the pressure ($P_2$) in the pilot pressure line multiplied by the $Area_{D2}$. At a dynamic equilibrium, where the exhalation valve is partially open and a continuous flow is passing through the exhalation valve, the force to open the valve is equal to the force to close the valve ($force_{open}=force_{close}$), so that a desired exhalation airway pressure $P_{aw}$ can be controlled by adjusting the pilot pressure $P_2$, since $P_{aw}$ is equal to $P_2 \times (Area_{D2}/Area_{aw})$. Conversely, the desired pilot pressure $P_2$ can be determined when a desired airway pressure $P_{aw}$ is known, since the pilot pressure $P_2$ is equal to $P_{aw} \times (Area_{aw}/Area_{D2})$.

Figure 2:
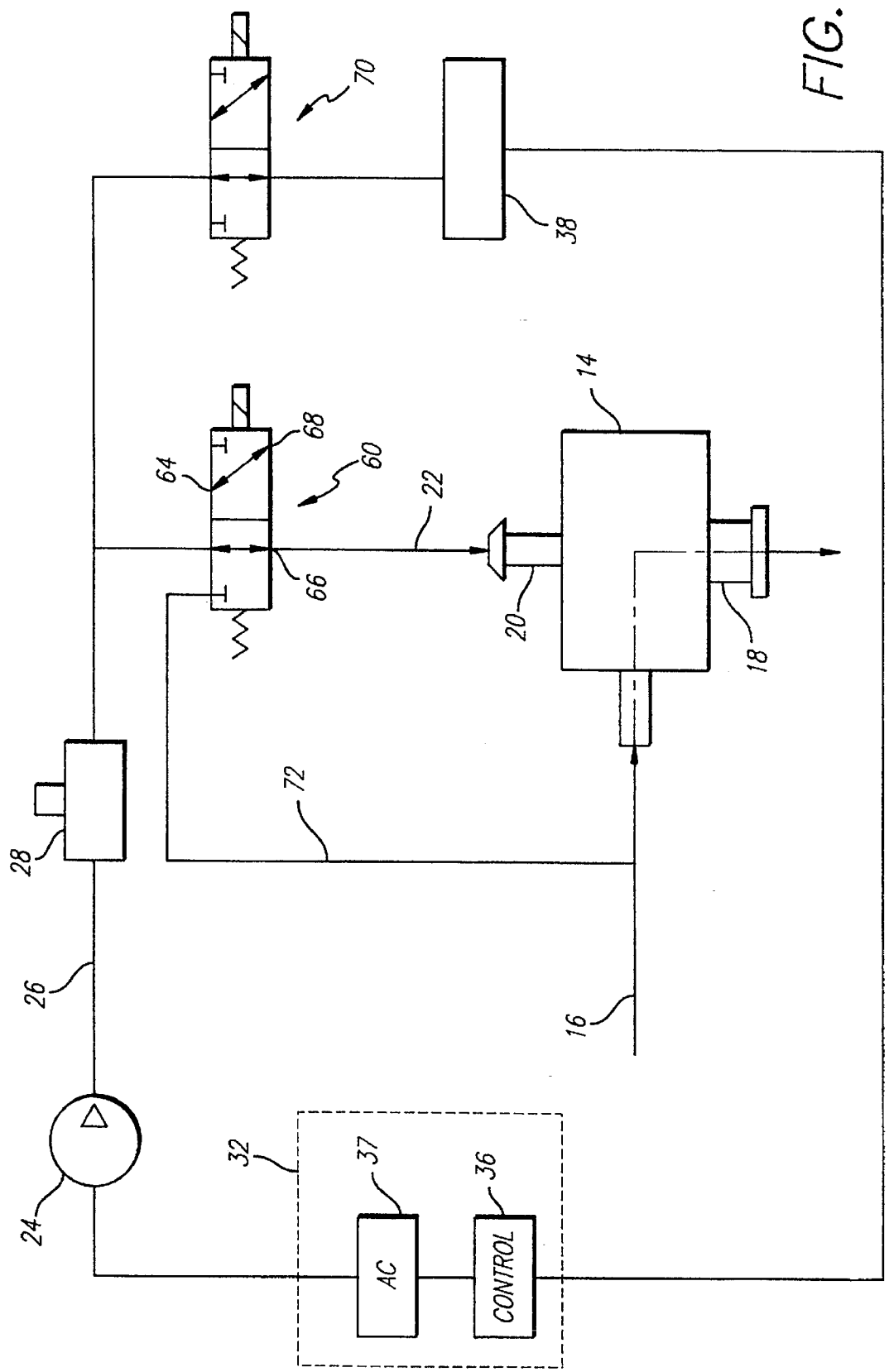
FIG. 2 is a diagram of a second embodiment of the apparatus of the invention for controlling a lung ventilator exhalation circuit.

An internal pneumatic pump 24, having an outlet line 26, is connected to the pilot pressure line 22 via a venturi 28, and is provided to generate a constant supply of pneumatic pressure for the pilot pressure line 22. The pneumatic pump is currently preferably a miniature vibrating armature pump for providing pressurized air, and is currently preferably energized and actuated by a sinusoidal electrical power signal, such as a 60 Hz power signal from a power supply 30 or 37, as is illustrated in FIG. 2. In one preferred aspect of the invention, the power signal is modulated by pump control means 32, which preferably comprises a pulse width modulation circuit 34, for generating a variable pulse duration actuation signal at a constant frequency to the pump. The pulse width modulation circuit is preferably connected to a control unit 36 accessible by an operator, or under programmable control, for controlling the pulse duration of the actuation signal. The control unit can be connected to a sensor or the ventilator system for input as to whether the ventilator is in an inspiration or exhalation portion of a breath cycle, for example, and can be connected to a pressure transducer 38, connected to the pump output through the venturi via line 40, to monitor the pressure of the pressurized air provided by the pump, and to provide feedback to the control unit to insure that the desired pneumatic pressure is achieved. Alternatively, other types of pumps can also be used as the pneumatic pump, such as a rotary vane pump, for example.

In a preferred aspect of the invention, the pneumatic pressure generated by the pump is also conveyed through line 44 to a reservoir 46 for storing pressurized air as a second source of pressurized air for operating the exhalation valve. The reservoir has a first inlet 48 in fluid communication with the pump through conduit 44, preferably including a one-way check valve 52, for receiving pressurized air from the pump. The reservoir also preferably includes a second inlet 54 in fluid communication with the exhalation circuit through conduit 56, also preferably including a one-way check valve 58, for receiving gas flow from the exhalation circuit so that the pressurized gas in the embodiment of FIG. 1. In this manner, the reservoir receives pressurized air at a pressure which is the greater of the pressure of air supplied by the pump and gas received from the exhalation circuit.

A main solenoid valve 60 is preferably provided in the pump conduit line, connected to receive pneumatic pressure from the pump through inlet 62 in a first position, and to receive pneumatic pressure through inlet 64 from the reservoir through line 65 in a second position. The main solenoid valve is currently preferably a two-way normally open solenoid valve connected to and controlled by the control unit. The main valve is connected in fluid communication with the exhalation valve to deliver pneumatic pressure to the pilot pressure line from the pump through outlet 66 in the first position, and to deliver pneumatic pressure through outlet 68 for operation of the exhalation valve in the second position. Thus, when the main valve is in the first position, pneumatic pilot pressure is delivered to the exhalation valve, and when the main valve is in the second position, pneumatic pilot pressure is delivered to the exhalation valve that has been stored in the reservoir, that is at a pressure that is the greater of the pressure of air supplied by the pump and gas received from the exhalation circuit.

A calibration solenoid valve 70 is also preferably connected to the pump pneumatic pressure line 40, for conveying pneumatic pressure generated by the pump. The calibration solenoid valve is also currently preferably a two-way normally open solenoid valve controlled by the control unit for periodically zeroing the pressure transducer 38.

During exhalation, the main solenoid valve 60 is switched to its first normally open position, to connect the pump output pressure through the venturi to the exhalation valve, to provide a stagnation or dynamic pressure to the exhalation valve as pilot pressure. Pneumatic pressure from the pump is also stored in the reservoir. The stagnation or dynamic pilot pressure is amplified in the exhalation valve by the area ratio of the exhalation valve to produce the baseline PEEP pressure during exhalation.

Figure 4:
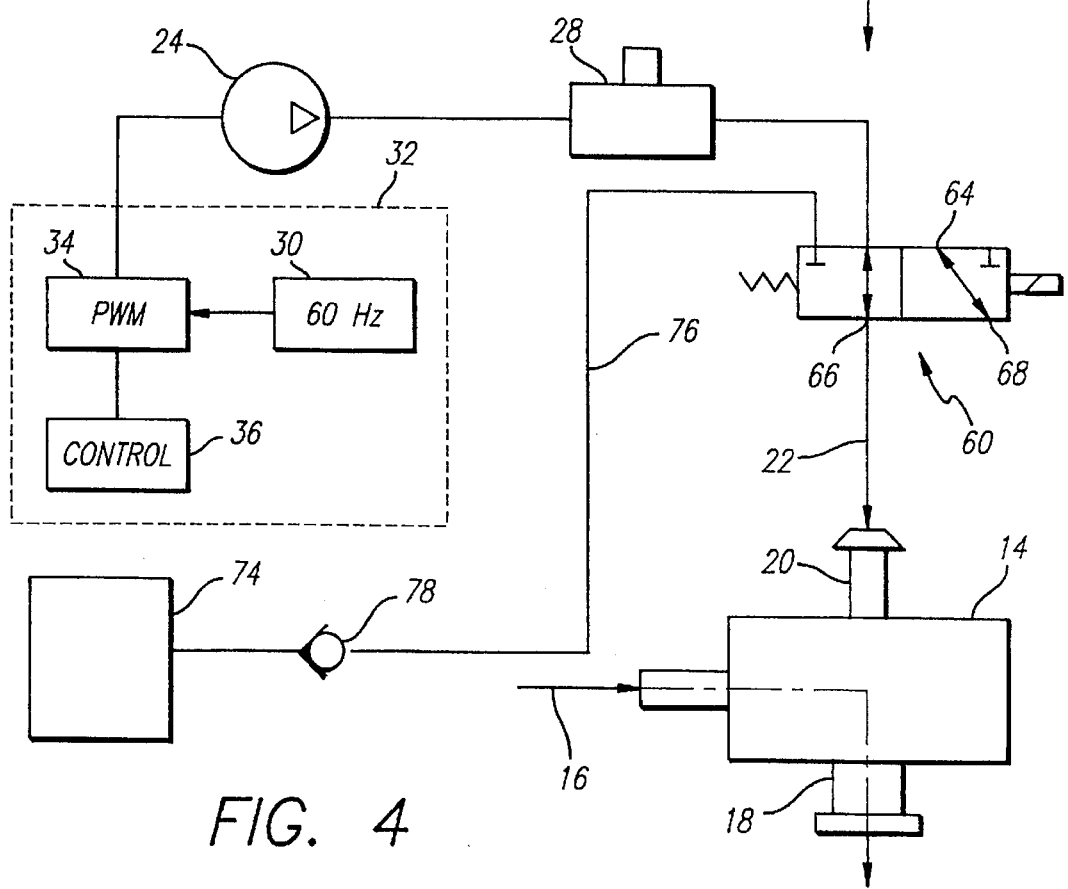
FIG. 4 is a diagram of a fourth embodiment of the apparatus of the invention for controlling a lung ventilator exhalation circuit.

During inspiration, the exhalation valve typically can not be closed by the pilot pressure provided by the relatively low level of flow provided by the pump, in comparison to the high level of pressure support provided in the patient airway, unless pilot air pressure is utilized from the pressure reservoir which has been stored as the highest of PEEP pressure or the pneumatic pressure provided by the pump, or alternatively, unless a sufficient pressure is available from a source 74 of pressurized breathing gas, as is illustrated in FIG. 4. Thus, as is illustrated in FIG. 1, during inspiration the main solenoid valve is switched to its second position, to connect the reservoir to the pilot pressure line of the exhalation valve. Pump pressure stored in the reservoir during exhalation can be used initially at the beginning of inspiration to close the exhalation valve, to raise the baseline pressure level for APRV, but when the patient airway pressure provided by the exhalation line of the ventilator exceeds the pump pressure stored in the reservoir, the one way valve 58 from the patient line opens, and the patient airway pressure is exerted as pilot pressure on the exhalation valve, to keep the exhalation valve closed in order to maintain the desired higher baseline pressure level during inspiration.

Elevated patient airway pressure which has been delivered during inspiration through the one way valve and the reservoir to the main valve to operate the exhalation valve, and that has become trapped in the line between the main valve and the exhalation valve, can be released through the venturi.

Figure 3:
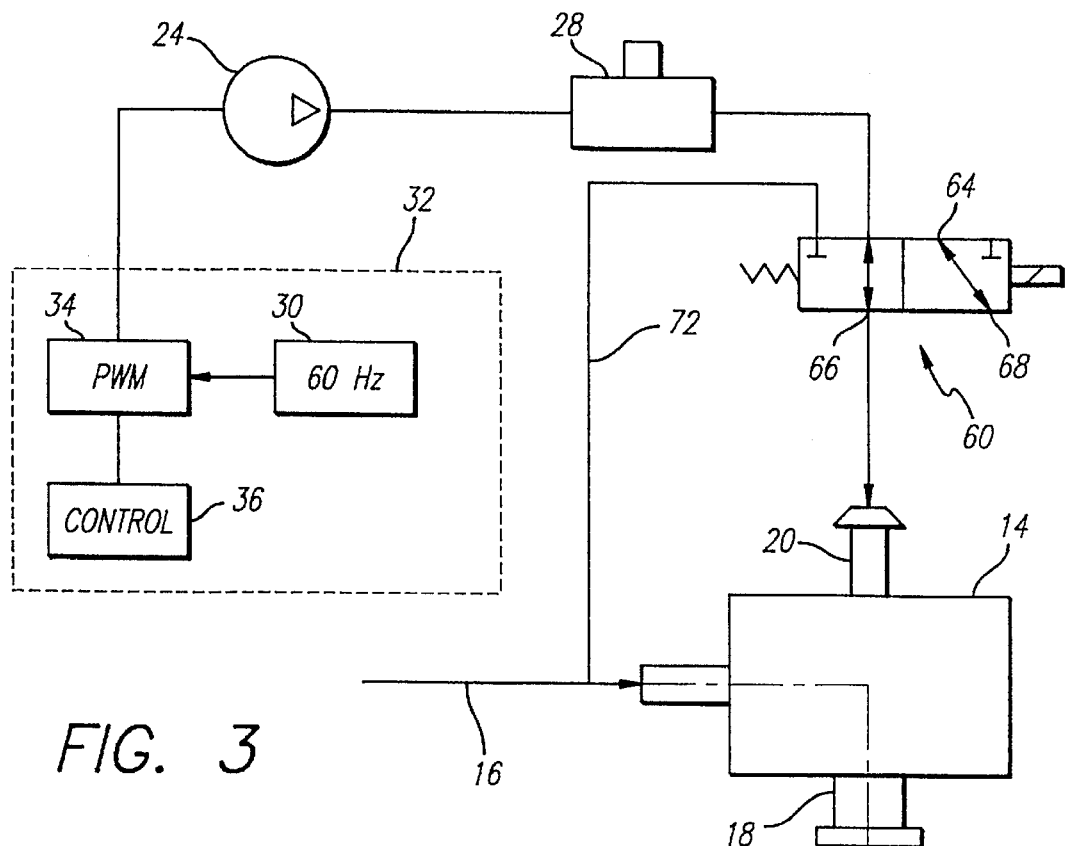
FIG. 3 is a diagram of a third embodiment of the apparatus of the invention for controlling a lung ventilator exhalation circuit.

As is illustrated in FIG. 2 and 3, in second and third preferred embodiments of the invention, the apparatus for controlling gas flow through an exhalation circuit of a lung ventilator need not include a reservoir, which can be replaced by a line 72 in fluid communication between the exhalation line 16 and the main solenoid valve, to be connected with inlet 64 of the valve when the valve is in a second position so that the exhalation line 16 can serve as a second source of pressurized gas for operation of the exhalation valve. Thus, during inspiration, when pressurized breathing gas is being delivered to the patient airway, the main valve can be switched to the second position, so that pressure from the exhalation line is delivered to the pilot pressure line for operation of the exhalation valve. Due to the area ratio of the exhalation valve, the exhalation will thus be caused to close, to stop inspired air from leaking through the exhalation valve. During exhalation, the main valve can be switched to the first position by cutting the power to the main valve, so that pneumatic pilot pressure from the pump is delivered through the main valve to operate the exhalation valve, and PEEP pilot pressure is connected to the exhalation valve, since the PEEP pilot pressure multiplied by the area ratio of the exhalation valve equals the PEEP pressure.

With reference to FIG. 3, in the third preferred embodiment of the invention, the apparatus for controlling gas flow through an exhalation circuit of a lung ventilator also need not include a pressure transducer or its associated solenoid valve, allowing for open loop control of the pump.

As mentioned above, in a fourth preferred embodiment of the invention illustrated in FIG. 4, a source of breathing gas 74, such as a cylinder of a piston ventilator for example, can be connected in fluid communication through a line 76 including a one way check valve 78 to the main solenoid valve, to be connected with inlet 64 of the main valve in a second position during inhalation, as a second source of pneumatic pilot pressure for operating the exhalation valve. Thus, during exhalation, pilot pressure for maintaining PEEP is provided by the relatively low level of flow provided by the pump, and during inspiration, pilot air pressure can be provided from pneumatic pressure available from a source 74 of pressurized breathing gas, such as a gas pressure cylinder of a piston or bellows ventilator, or a proportional solenoid ventilator, for example.

The present invention also provides for a method of controlling gas flow through the exhalation circuit of the lung ventilator for controlling patient airway pressure. According to the method of the invention, the pressure of pressurized air supplied by the pump is controlled, so as to maintain PEEP. The main valve is switched between the first and second positions, such that when the main valve is in the first position, the exhalation valve is operated solely by pilot pressure supplied by the pump, and such that when the main valve is in the second position, the exhalation valve is operated by a pilot pressure from the second source of pressurized air. In one preferred embodiment illustrated in FIG. 1, the second source of pressurized air is a reservoir that provides the greater of the pressure of the pressurized air supplied by the pump and the pressure of the gas flow from the exhalation circuit. The main valve is preferably switched to the first position during an exhalation portion of a breathing cycle of the ventilator, and is preferably switched to the second position during an inhalation portion of a breathing cycle of the ventilator. In the embodiment illustrated in FIGS. 1, 3 and 4, the step of controlling the pressure of pressurized air supplied by the pump comprises generating a variable pulse duration actuation power signal for actuating the pump, and controlling the duration of the variable pulse duration actuation signal.

It has thus been demonstrated that the present invention provides for a method and apparatus for controlling patient airway baseline pressure levels in a ventilator with a limited supply of pneumatic pressure, and having a pneumatically controlled exhalation valve, by supplying an internal source of controllable pilot pressure for operating the exhalation valve. With the method and apparatus of the invention, control of PEEP is possible in any ventilator having a limited supply of pneumatic pressure, such as a piston type or bellows type ventilator, without the use of an external source of pressurized air. The system can be electrically controlled and can be employed by most ventilator systems utilizing pneumatically controlled exhalation valves, including piston type ventilator systems and bellows type ventilator systems, to give the ventilator the capability of generating and changing the level of PEEP, such as for providing APRV.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for controlling gas flow through an exhalation circuit of a lung ventilator for controlling airway pressure in a patient airway connected to the exhalation circuit, comprising:

a pneumatically operated exhalation valve for controlling flow of gas through said exhalation circuit;

a pump for supplying a first source of pressurized air;

a second source of pressurized air;

a pump control for controlling the pressure of pressurized air supplied by said pump means;

a valve connected to said pump and said second source of pressurized air, said valve having a first position in fluid communication with said pump for receiving pressurized air from said pump, and a second position in fluid communication with said second source of pressurized air for receiving pressurized air from said second source of pressurized air, said valve having an outlet connected to a pilot pressure line in fluid communication with said exhalation valve to deliver pressurized air through said pilot pressure line to said exhalation valve for operation of said exhalation valve; and a valve control for switching said valve between said first and second positions.

2. The apparatus of claim 1, wherein said pump control means comprises pulse width modulation means for generating a variable pulse duration actuation signal to said pump means, and means for controlling the pulse duration of said actuation signal to control said pump means.

3. The apparatus of claim 1, wherein said second source of pressurized air comprises a reservoir for storing and supplying pressurized air, said reservoir having a first inlet in fluid communication with said pump means for receiving pressurized air from said pump means, a second inlet in fluid communication with said exhalation circuit for receiving gas flow from said exhalation circuit, and an outlet connected in fluid communication with said valve means for supplying pressurized air through said pilot pressure line to said exhalation valve.

4. The apparatus of claim 1, wherein said second source of pressurized air comprises said exhalation circuit.

5. The apparatus of claim 1, wherein said control means comprises pressure sensor means for sensing the pressure of said pressurized air supplied by said pump means.

6. The apparatus of claim 3, wherein said reservoir first and second inlets each include a check valve permitting flow of the greater pressure of pressurized air into said reservoir from said pump means and said exhalation circuit, such that when said valve means is in said second position, pressurized air is delivered through said reservoir outlet to said valve means at the greater pressure of said pressurized air supplied by said pump means or said gas flow from said exhalation circuit.

7. In a method of controlling gas flow through an exhalation circuit of a lung ventilator for controlling patient ventilator including a pneumatically operated exhalation valve for controlling flow of gas through the exhalation circuit; providing pump means for supplying a first source of pressurized air; providing a second source of pressurized air; and providing valve means connected in fluid communication with said pump means in a first position, and connected in fluid communication with said exhalation circuit in a second position, said valve means being connected to deliver pressurized air to said exhalation valve to control said exhalation valve, the improvement comprising the steps of:

controlling the pressure of pressurized air supplied by said pump means; and switching said valve means between said first and second positions, such that when said valve means is in said first position, said exhalation valve is operated by pilot pressure supplied by said pump means, and when said valve means is in said second position, said exhalation valve is operated by pilot pressure from said second source of pressurized air.

8. The method of claim 7, wherein said step of switching said valve means comprises switching said valve means to said first position during an inhalation portion of a breathing cycle of said ventilator.

9. The method of claim 7, wherein said step of switching said valve means comprises switching said valve means to said second position during an exhalation portion of a breathing cycle of said ventilator.

10. The method of claim 7, wherein said step of controlling the pressure of pressurized air supplied by said pump means comprises generating a variable pulse duration actuation signal for actuating said pump means, and controlling the duration of said variable pulse duration actuation signal.

* * * * *

UNITED STATES PATENT AND TRADEMARK OFFICE
CERTIFICATE OF CORRECTION

PATENT NO. : 5,632,270
DATED : May 27, 1997
INVENTOR(S) : John J. O'Mahony, Floyd R. Farnham, III It is certified that error appears in the above-indentified patent and that said Letters Patent is hereby corrected as shown below:

Column 1, line 58, after "patients.", and before "patients,", add --For such--.

Column 4, line 53, after "so that the", add --exhalation line 16 also comprises a part of the second source of--.

Column 8, Claim 7, line 14, after "controlling patient", add--airway pressure, including the step of providing a lung--.

Signed and Sealed this

Ninth Day of December, 1997

BRUCE LEHMAN

*Attest:*

*Attesting Officer*  *Commissioner of Patents and Trademarks*